(12) United States Patent
Sauter

(10) Patent No.: US 10,016,216 B2
(45) Date of Patent: Jul. 10, 2018

(54) SURGICAL PROTECTIVE DEVICE FOR A SURGICAL SEALING ELEMENT AND SURGICAL SEALING SYSTEM

(71) Applicant: Aesculap AG, Tuttlingen (DE)

(72) Inventor: Wolfgang Sauter, Renquishausen (DE)

(73) Assignee: Aesculap AG, Tuttlingen (DE)

( * ) Notice: Subject to any disclaimer, the term of this patent is extended or adjusted under 35 U.S.C. 154(b) by 510 days.

(21) Appl. No.: 14/657,069

(22) Filed: Mar. 13, 2015

(65) Prior Publication Data
US 2015/0196322 A1 Jul. 16, 2015

Related U.S. Application Data

(63) Continuation of application No. PCT/EP2013/069247, filed on Sep. 17, 2013.

(30) Foreign Application Priority Data

Sep. 19, 2012 (DE) .......................... 10 2012 108 809

(51) Int. Cl.
*A61B 1/00* (2006.01)
*A61B 17/34* (2006.01)

(52) U.S. Cl.
CPC .. *A61B 17/3462* (2013.01); *A61B 2017/3464* (2013.01); *F04C 2270/0421* (2013.01)

(58) Field of Classification Search
CPC ........ A61B 17/3462; A61B 2017/3464; A61B 2017/3466; A61M 39/0247; A61M 2039/027; A61M 2039/0273; A61M 2039/0279
See application file for complete search history.

(56) References Cited

U.S. PATENT DOCUMENTS

| 7,901,380 | B2 | 3/2011 | Ross |
| 8,202,252 | B2 | 6/2012 | Ross |
| 2005/0070851 | A1 | 3/2005 | Thompson et al. |
| 2006/0135977 | A1* | 6/2006 | Thompson ......... A61B 17/3462 606/185 |
| 2009/0326463 | A1 | 12/2009 | Ross |
| 2010/0274193 | A1 | 10/2010 | Patton et al. |
| 2011/0124973 | A1 | 5/2011 | Ross |
| 2011/0251560 | A1 | 10/2011 | Albrecht et al. |

FOREIGN PATENT DOCUMENTS

| DE | 20 2008 009 527 | 11/2008 |
| EP | 2 138 112 | 5/2011 |
| JP | 2001128985 | 5/2001 |

* cited by examiner

*Primary Examiner* — Jonathan Miles
*Assistant Examiner* — Wade Miles
(74) *Attorney, Agent, or Firm* — Lipsitz & McAllister, LLC

(57) ABSTRACT

The invention relates to a surgical protective device for a surgical sealing element of a surgical sealing system comprising a trocar sleeve, the surgical sealing element having an expandable insertion opening. Said protective device comprises a ring-shaped or substantially ring-shaped main body adapted to be arranged on the trocar sleeve, on a part thereof or on the sealing element and defines a through-opening with a plurality of protective elements arranged in the circumferential direction and extending parallel to or pointing towards a longitudinal axis of the protective device. Each of the protective elements is configured asymmetrically in relation to a plane containing a longitudinal axis defined by the main body.

19 Claims, 8 Drawing Sheets

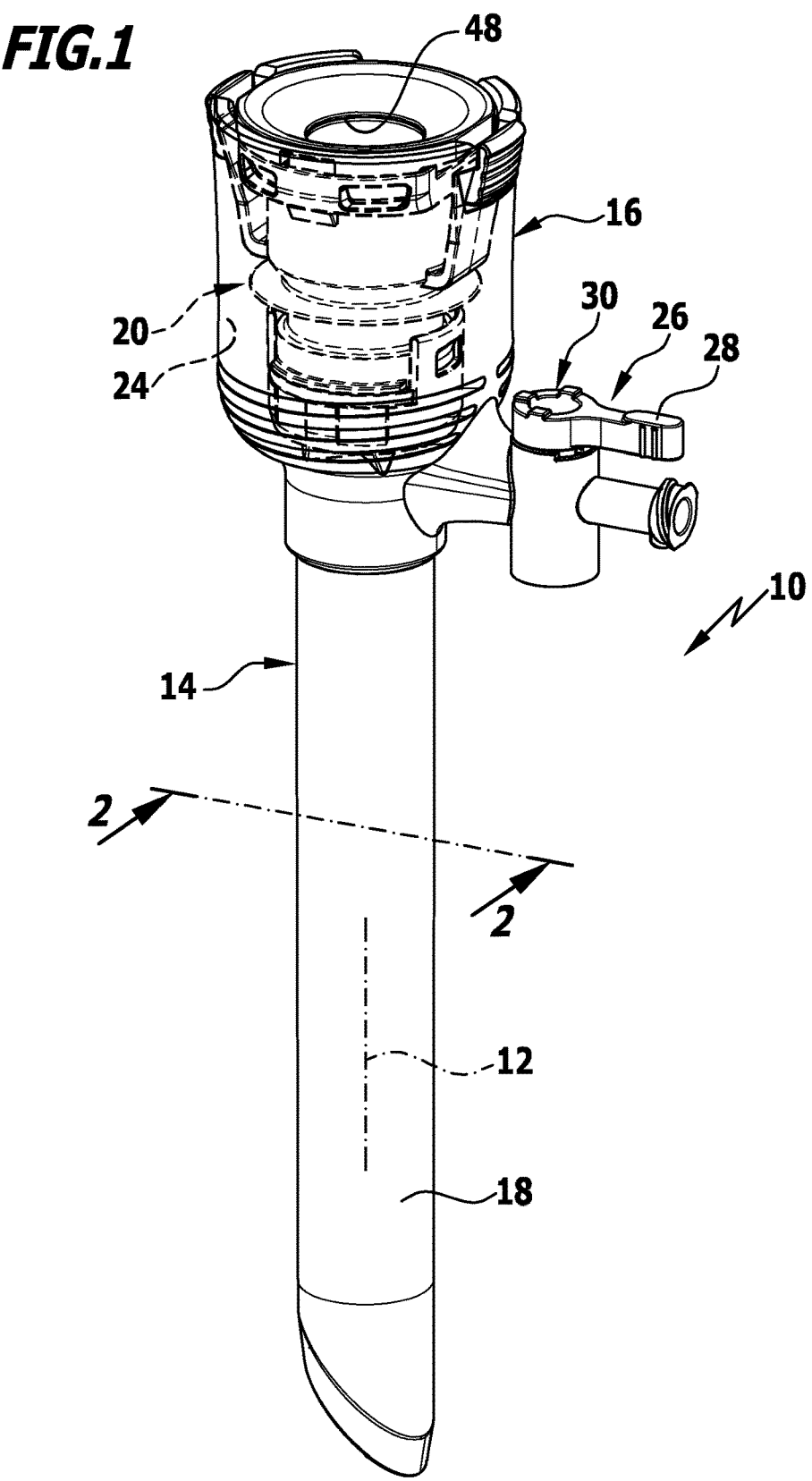

SURGICAL PROTECTIVE DEVICE FOR A SURGICAL SEALING ELEMENT AND SURGICAL SEALING SYSTEM

CROSS-REFERENCE TO RELATED APPLICATIONS

This application is a continuation of international application number PCT/EP2013/069247 filed on Sep. 17, 2013 and claims the benefit of German application number 10 2012 108 809.8 filed on Sep. 19, 2012, which are incorporated herein by reference in their entirety and for all purposes.

FIELD OF THE INVENTION

The present invention relates to surgical protective devices for surgical sealing elements of surgical sealing systems generally, and more specifically to a surgical protective device for a surgical sealing element of a surgical sealing system comprising a trocar sleeve, the surgical sealing element having an expandable insertion opening, the protective device having a ring-shaped or substantially ring-shaped main body adapted to be arranged on the trocar sleeve, on a part thereof or on the sealing element and defining a through-opening with a plurality of protective elements arranged in the circumferential direction and extending parallel to or pointing towards a longitudinal axis of the protective device.

The invention also relates to surgical sealing systems generally, and more specifically to a surgical sealing system comprising a trocar sleeve, a surgical sealing element held on the trocar sleeve or on a part thereof and having an expandable insertion opening, for sealing the insertion opening when inserting a surgical instrument, and a surgical protective device for the sealing element.

BACKGROUND OF THE INVENTION

A surgical protective device and a surgical sealing system are known, for example, from DE 20 2008 009 527 U1. The protective device serves to prevent damage to the sealing element of the sealing system when inserting surgical instruments or an obturator for closing the trocar sleeve. Both manufacture and positioning of the protective device on or in the seal present a problem in that with all protective devices comprising a plurality of protective elements, these have to be arranged so as to overlap in order that the protective device can be brought into contact with an inner side of the sealing element.

SUMMARY OF THE INVENTION

In a first aspect of the invention, a surgical protective device for a surgical sealing element of a surgical sealing system comprising a trocar sleeve, the surgical sealing element having an expandable insertion opening. Said protective device comprises a ring-shaped or substantially ring-shaped main body adapted to be arranged on the trocar sleeve, on a part thereof or on the sealing element and defines a through-opening with a plurality of protective elements arranged in the circumferential direction and extending parallel to or pointing towards a longitudinal axis of the protective device. Each of the protective elements is configured asymmetrically in relation to a plane containing a longitudinal axis defined by the main body.

In a second aspect of the invention, a surgical sealing system comprises a trocar sleeve, a surgical sealing element held on the trocar sleeve or on a part thereof and having an expandable insertion opening, for sealing the insertion opening when inserting a surgical instrument, and a surgical protective device for the sealing element. Said protective device comprises a ring-shaped or substantially ring-shaped main body adapted to be arranged on the trocar sleeve, on a part thereof or on the sealing element and defines a through-opening with a plurality of protective elements arranged in the circumferential direction and extending parallel to or pointing towards a longitudinal axis of the protective device. Each of the protective elements is configured asymmetrically in relation to a plane containing a longitudinal axis defined by the main body.

BRIEF DESCRIPTION OF THE DRAWING FIGURES

The foregoing summary and the following description may be better understood in conjunction with the drawing figures, of which:

FIG. 1 shows a perspective overall view of a surgical sealing system comprising a trocar sleeve;

DETAILED DESCRIPTION OF THE INVENTION

Figure 2A:
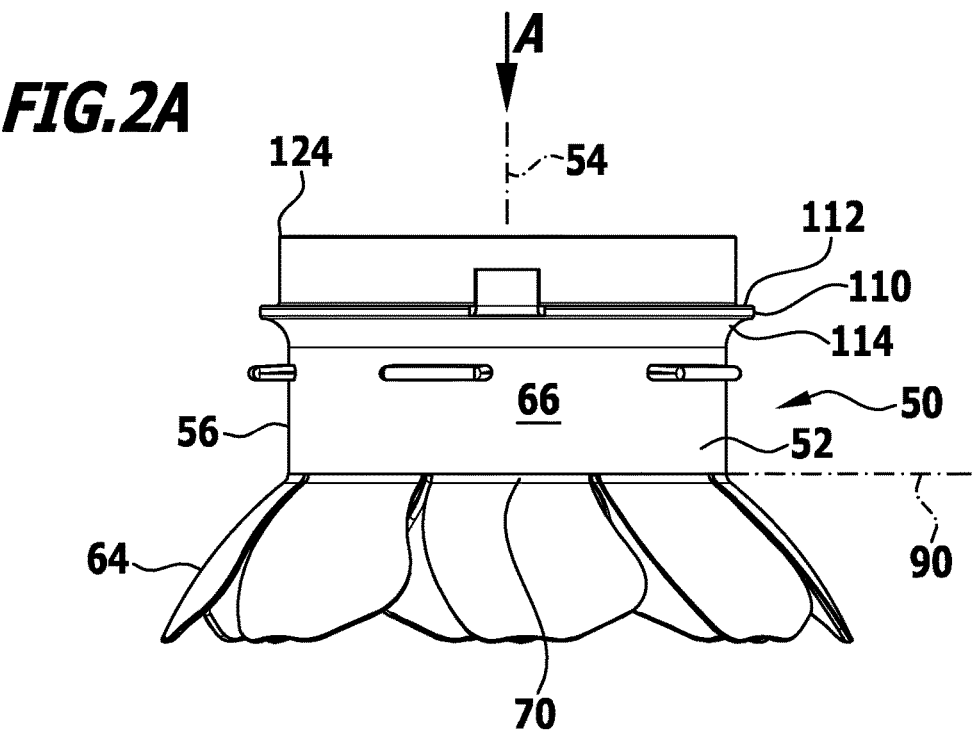
FIG. 2A shows a side view of a surgical protective device in an initial position after manufacture.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical protective device for a surgical sealing element of a surgical sealing system comprising a trocar sleeve, the surgical sealing element having an expandable insertion opening, said protective device comprising a ring-shaped or substantially ring-shaped main body adapted to be arranged on the trocar sleeve, on a part thereof or on the sealing element and defining a through-opening with a plurality of protective elements arranged in the circumferential direction and extending parallel to or pointing towards a longitudinal axis of the protective device, wherein each of the protective elements is configured asymmetrically in relation to a plane containing a longitudinal axis defined by the main body.

On the one hand, the asymmetrical configuration of the protective elements ensures, in particular, that the sealing element is securely covered and, on the other hand, in particular, also prevents the creation of an unnecessarily high or thick package of material due to several overlappings. The positioning of the protective elements on top of each other for overlapping purposes is, in particular, also simplified by the asymmetrical shape of the protective elements.

The protective device is particularly easy and safe to handle when the main body is configured substantially in the form of a ring-shaped sleeve. The sleeve can then define, for example, a maximum inner diameter which can be sealed by the sealing element. In other words, no instruments having a larger outer diameter than the inner diameter of the main body can be inserted through the sealing system.

A particularly simple and safe overlapping of the protective elements can be achieved, in particular, by the protective elements being slightly convexly curved facing away from the longitudinal axis. In particular, a curvature of the protective elements can correspond to a curvature of a wall of the sleeve defining the main body.

The protective elements expediently have first ends which are arranged on the main body. In particular, second or free ends of the protective elements can then be freely moved relative to the main body. The protective elements are preferably arranged on an edge surface of the main body that faces in the distal direction. In this way, a particularly compact construction of the protective device can be produced.

To achieve maximum movability of the protective elements relative to the main body, it is advantageous for the first ends of the protective elements not to overlap.

It is expedient for the first ends of the protective elements to be spaced from one another. Movability of the protective elements relative to the main body can thereby be increased.

A spacing between the first ends of adjacent protective elements preferably corresponds at least to a thickness of the protective elements and/or of the main body. With such a spacing of the first ends of adjacent protective elements from one another it can be ensured that as great movability as possible, in particular, a swiveling capability, of the protective elements in the direction towards the longitudinal axis is possible.

The first ends of the protective elements expediently define a circular arc segment. In particular, they can, therefore, be formed directly as an extension of a wall of the sleeve.

It is advantageous for the first ends of the protective elements to be arranged concentrically with the longitudinal axis. In particular, this allows the sleeve-shaped main body of the protective device to be extended by the protective elements, as it were, in the distal direction.

Manufacture of the protective device is simplified if, in an initial position after manufacture, the protective elements project in the radial direction facing away from the longitudinal axis over the edge surface facing in the distal direction. In particular, the protective device can be constructed such that the protective elements do not overlap in the initial position. The protective device can then be produced, for example, in the desired way and in a defined manner from a plastic material by injection molding.

To enable optimum positioning of the protective elements on the sealing element to be protected, it is advantageous for the protective elements to be formed in the shape of lamellas having a thickness corresponding at the most to a thickness of the sleeve defining the main body.

Both the construction and the manufacture of the protective device can be further simplified, in particular, by all of the protective elements being identically constructed.

In accordance with a further preferred embodiment of the invention, it may be provided that each protective element has two edges extending away from the first end, that the one edge is convexly curved facing away from the protective element, and that the other edge is concavely curved facing away from the protective element. In this way, it is possible to construct in a defined manner asymmetrical protective elements which enable optimized overlapping in comparison with the state of the art, more particularly, irrespective of how far the sealing element is open in dependence upon a diameter of an inserted instrument.

In principle, it is conceivable to arrange or form adjacent protective elements mirror-symmetrically in relation to a plane containing the longitudinal axis. It is, however, advantageous for the convexly curved edges of the protective elements, in the initial position, to face towards the concavely curved edges of directly adjacent protective elements. In this way, in particular, a spacing between the convexly and concavely curved edges of adjacent protective elements can be minimized, more particularly, already in the initial position. In particular, an overlapping of adjacent protective elements can also be thereby optimized, for example, also with the effect that a multiple overlapping of protective elements, i.e., more than two overlapping protective elements, is avoided. In particular, this means that a radial beam emanating from the longitudinal axis never penetrates more than, for example, two protective elements.

As mentioned above, for the manufacture of the protective device it is advantageous for the protective elements not to overlap in the initial position.

It is expedient for the protective elements to have a second, in particular, free, end facing away from the main body. In particular, this configuration makes a movability possible, which is required for use of the protective device.

The second end advantageously extends between the edges extending away from the first end. The second end of the protective elements, therefore, lies, in particular, substantially opposite the first end. The convexly and concavely curved edges of the protective elements, therefore, form lateral delimitations.

It is expedient for the second end to define an end edge surface essentially having a slightly convexly curved basic shape facing away from the main body, and for the end edge surface to have a concavely curved edge section facing away from the main body. In particular, this configuration has the advantage that the concavely curved edge section can face the longitudinal axis when the protective elements are swiveled in the direction towards the longitudinal axis, so that the concavely curved edge sections of all protective elements can together form a substantially circular opening of the protective device, which then surrounds the longitudinal axis.

A width of the protective elements parallel to a plane containing the first ends preferably increases from the first end in the direction towards the second end. In particular, irrespective of a position of the protective elements, i.e., in particular, irrespective of a swiveling of the protective elements relative to the main body towards the longitudinal axis, a defined overlapping can thereby be achieved, in order to always safely protect the sealing element of the sealing system. In particular, this configuration has the advantage that safe overlapping and, therefore, protection of the sealing element are also ensured when instruments with a very large diameter are inserted through the sealing system.

In principle, it is conceivable for the width of the protective elements to increase right up to the second end. It is, however, advantageous for the width of the protective elements to have a maximum between the first end and the end edge surface. Such a configuration enables, in particular, a shape of the protective elements to be created, which irrespective of a swivel position of the protective elements relative to the main body always ensures only an overlapping of adjacent protective elements.

The overlapping may, in particular, be further optimized by the maximum of the width of the protective elements being closer to the second end than to the first end of the protective elements. In particular, also with very large instrument diameters, an overlapping and, therefore, a protection of the sealing element can thereby be guaranteed.

To achieve optimal movability between the protective elements and the main body, it is expedient for the protective elements to be connected or coupled in an area of transition to the main body in an articulated and/or hinge-like manner to the main body.

The protective device is particularly easy to manufacture when the protective elements and the main body are connected to one another by a film hinge. In particular, the protective device can then also be constructed in one piece.

The protective elements are preferably adapted to be swiveled from the initial position to a protective position in the direction towards the longitudinal axis. In particular, a defined movability between the protective elements and the main body can thereby be enabled.

Adjacent protective elements expediently overlap partially in a protective position. Protection of the sealing element can thereby be ensured irrespective of a swiveled position of the protective elements in the direction towards the longitudinal axis. In particular, the protective elements can point in the direction towards the longitudinal axis in the protective position. However, in the protective position, the protective elements can, in particular, define different swivel angles between them and the main body, the swivel angle depending upon a diameter of the instrument inserted into the sealing system and upon a direction of insertion thereof in relation to the longitudinal axis of the sealing system.

In accordance with a further preferred embodiment of the invention, it may be provided that the protective elements, in the protective position, define at the most a joint maximum inner diameter corresponding to an inner diameter of the main body. In this way, it can be ensured that also when inserting instruments with an outer diameter corresponding substantially to the inner diameter of the main body, the sealing element is still completely or substantially completely protected by the protective elements of the protective device.

Furthermore, it is advantageous for the protective elements, in the protective position, to define a minimal inner diameter when they overlap to the maximum extent, and for the concavely curved edge sections of the end edge surfaces to then be aligned concentrically or substantially concentrically with the longitudinal axis and to be maximally close thereto. The protective elements, therefore, define in a maximally overlapping protective position an opening delimited by the concavely curved edge sections of the end edge surfaces, which then preferably defines an inner diameter corresponding to a smallest inner diameter of the sealing element. The sealing element in the unexpanded state, i.e., without an instrument inserted into the sealing system, is, therefore, protected to the maximum extent.

To avoid unnecessarily high packages of material when the protective device is in use, it is expedient for the protective elements, in the protective position, irrespective of which inner diameter they define with their second ends, to only overlap to such an extent that solely adjacent protective elements lie on top of each other. In this way, in particular, a triple overlapping of protective elements and an overlapping of even more protective elements can be avoided.

An opening defined by the second ends of the protective elements can, in particular, be opened with particularly low force expenditure when the concavely curved edge of the protective elements covers the convexly curved edge on an outer side of the directly adjacent protective element that faces away from the longitudinal axis or vice versa. In other words, for example, the concavely curved edge of a protective element can abut on the inside or the outside on the adjacent protective element. This condition has to be fulfilled to an equal extent for all protective elements of the protective device. Furthermore, if the protective elements optionally have a fiction-reducing outer surface, for example, owing to application of a corresponding coating, opening and closing of the protective device can then be further facilitated.

For attaching the protective device to the sealing system, it is advantageous for it to have a connecting device arranged on the main body for connecting the protective device to the surgical sealing element or to the surgical sealing system. In other words, the protective device can be connected, in particular, directly to the sealing element and via the latter indirectly to a sealing element retainer of the sealing system, for example, in a permanently undetachable or only temporary manner.

A particularly simple coupling of the protective device to the sealing element or to the sealing system can, in particular, be achieved by the connecting device comprising at least one connecting element projecting in the radial direction from the main body.

To enable as stable and defined a connection as possible to be established between the protective device and the sealing element or the sealing system, it is expedient for a plurality of connecting elements spaced from one another in the circumferential direction to be provided.

The connecting elements are advantageously arranged so as to be uniformly distributed over the circumference of the main body. Forces acting upon the protective device can then be uniformly transmitted to the sealing element or the sealing system.

Furthermore, it may be expedient for the protective elements to have a constant thickness along their extent and/or to be of inherently flexible construction. They are then able to abut, in particular, also over a large area, on an inner side of the sealing element of the sealing system.

Manufacture of the protective device is significantly simplified when it is of one-piece construction. The need for the protective elements to be individually connected to the main body can then be eliminated.

To enable use of the protective device in a sterile space, it is expedient for the protective device to be produced from a sterilizable material.

The protective device is expediently produced from a plastic material. The protective device can be easily produced from a plastic material, in particular, by injection molding. It is advantageous for the plastic material to preferably be a thermoplastic material.

The present invention further relates to a surgical sealing system comprising a trocar sleeve, a surgical sealing element held on the trocar sleeve or on a part thereof and having an expandable insertion opening, for sealing the insertion opening when inserting a surgical instrument, and a surgical protective device for the sealing element, wherein the protective device comprises a ring-shaped or substantially ring-shaped main body adapted to be arranged on the trocar sleeve, on a part thereof or on the sealing element and defines a through-opening with a plurality of protective elements arranged in the circumferential direction and extending parallel to or pointing towards a longitudinal axis of the protective device, wherein each of the protective elements is configured asymmetrically in relation to a plane containing a longitudinal axis defined by the main body.

The sealing system, therefore, comprises a protective device which ensures protection of the sealing element of the sealing system in an optimal way. In particular, the sealing system, therefore, also has the advantages described above in conjunction with preferred embodiments of protective devices.

It is expedient for the sealing element to be configured to seal shafts of elongate surgical instruments when inserted into the body of a human being or an animal, to define a longitudinal axis and to have an opening which is variable in diameter and is oriented transversely or substantially transversely to the longitudinal axis and through which a shaft is insertable. In particular, gas can then be prevented from escaping from a patient's body when an instrument is inserted into the patient's body through the trocar sleeve or is located therein.

It is advantageous for the sealing element to have a flexible wall closed in ring-shaped configuration, for the wall to have a first and a second edge, each closed within itself, and for the first edge to delimit the opening. In particular, elongate shafts, preferably with a circular cross section, can be optimally sealed with such a sealing element.

To enable the protective device to be removed from the sealing element, when required, it is expedient for the protective device to be detachably connectable to the sealing element.

In accordance with a further preferred embodiment of the invention, it may be provided that a connecting device for connecting the protective device to the surgical sealing element or to the surgical sealing system is arranged on the main body, and that the sealing element comprises connecting members corresponding to the connecting device. When, for example, the connecting device is configured in the form of connecting projections, it is expedient for the sealing element to have connecting receptacles corresponding thereto.

A trocar system forming a surgical sealing system, designated in its entirety by reference numeral 10, is illustrated schematically in FIGS. 1 to 6. It comprises a trocar sleeve 14 defining a longitudinal axis 12 with a sealing housing 16 and a shaft 18 extending in the distal direction away from the sealing housing 16, a sealing assembly 20 arranged in the sealing housing 16 and optionally an obturator 22, shown schematically in FIG. 6, for separating and opening out body tissue. Prior to insertion of the trocar sleeve 14 into a patient's body, the obturator 22 is inserted into the trocar sleeve 14, as shown schematically in FIG. 6, in order to facilitate insertion of the trocar sleeve 14 into the patient's body.

The trocar sleeve 14 defines a receptacle 24 for the sealing assembly 20 in the interior of the sealing housing 16. Arranged in the area of transition between the sealing housing 16 and the shaft 18 is a Luer lock connector 26 projecting transversely from the longitudinal axis 12, by means of which a fluid connection can be established into the interior of the shaft 18. Furthermore, arranged on the Luer lock connector 26 is a closing valve 30 which is provided with a swivel lever 28 for actuation.

The sealing assembly 20 comprises two seals, namely a cross-slot valve 32 held on a retaining ring 34 coupled to a sealing element retainer 44, and a sealing element 36 having a substantially circular insertion opening 38 at its distal end. A proximal end, in the form of a flange 40, of the sealing element 36 is held in a clamping manner between an edge surface 42 of the sealing element retainer 44 facing in the proximal direction and a cover 46. The cover 46 has a circular opening 48 which defines a maximum outer diameter for instrument shafts insertable into the trocar sleeve 14.

After connection with the cross-slot valve 32, insertion of the sealing element 36 from the proximal end and fixing thereof by means of the cover 46, the sealing element retainer 44 is insertable from the proximal end into the sealing housing 16 and detachably connectable in a latching manner thereto.

A protective device, designated in its entirety by reference numeral 50, serves to protect the sealing element 36. The protective device is shown schematically in FIGS. 2A to 2C in an initial position which it assumes directly after manufacture. In particular, the protective device 50 can be produced in one piece from a sterilizable plastic material by injection molding.

The protective device 50 comprises a main body 52, which is essentially configured in the form of a short sleeve 56 defining a longitudinal axis 54. At a ring-shaped edge surface 58 facing in the distal direction, a plurality of protective elements 60 are articulatedly connected to the sleeve 56. In the embodiment shown in the Figures, there are eight protective elements 60. The protective elements 60 are configured in the form of thin lamellas 62 which have a thickness which corresponds at the most to a wall thickness of the sleeve 56. An outer side 64 of the protective elements 60, facing away from the longitudinal axis 54, is slightly convexly curved. A curvature of the outer side 64 preferably corresponds to a curvature of an outer side 66 of the sleeve 56.

In the initial position directly after manufacture, the protective elements 60 project in the radial direction facing away from the longitudinal axis 54 over the edge surface 58 facing in the distal direction. It is therefore possible for the protective device 50 to be manufactured in a clean manner and without any burrs connecting the protective elements 60 to one another by injection molding. All of the protective elements 60 are of identical construction and are arranged so as to be uniformly distributed over the circumference of the edge surface 58. However, the protective elements 60 are spaced slightly from one another.

A spacing 68 between first ends 70 of the protective elements 60, which are connected to the edge surface 58 of the main body 52, corresponds at least to a wall thickness thereof, i.e., to a thickness of the sleeve 56.

The protective elements 60 are all asymmetrically configured in relation to a plane 72 containing the longitudinal axis 54. Each protective element 60 has two edges 74 and 76 extending away from the first end 70, the edge 74 being convexly curved facing away from the protective element 60, and the edge 76 being concavely curved facing away from the protective element 60. All of the convexly curved edges 74 of the protective elements 60 point, in the initial position, towards the concavely curved edges 76 of directly adjacent protective elements 60. In the initial position, the protective elements 60 do not overlap, as shown schematically in FIGS. 2A to 2C. Furthermore, the edges 74 and 76 of adjacent protective elements 60 do not touch each other in the initial position, but are spaced at a distance from each other which corresponds at least to the size of the spacing 68.

All of the protective elements 60 have a second end 78 which faces away from the main body 52. The second end 78 extends between the edges 74 and 76, which continue via rounded parts 80 and 82, respectively, into the second end 78. The second end 78 defines an end edge surface 84 which faces away from the main body 52. It may be straight-lined or optionally be slightly convexly curved facing away from the main body 52, i.e., have a slightly convexly curved basic shape.

Furthermore, the end edge surface 84 may optionally comprise a concavely curved edge section 86 facing away from the main body 52. In particular, this may extend along a length of the end edge surface 84 which corresponds approximately to half of the length between the rounded parts 80 and 82.

A width 88 of the protective elements 60 parallel to a plane 90 containing the first ends 70 increases from the first end 70 of each protective element 60 in the direction towards the second end 78. FIG. 2C shows schematically the width 88a at the first end 70, and a maximum width 88b, which may also be referred to as a maximum of the width 88 of the protective element 60, each protective element having such a maximum of the width 88 between the first end 70 and the end edge surface 84. The maximum width 88b of each protective element 60 is closer to the second end 78 than to the first end 70.

Figure 2B:
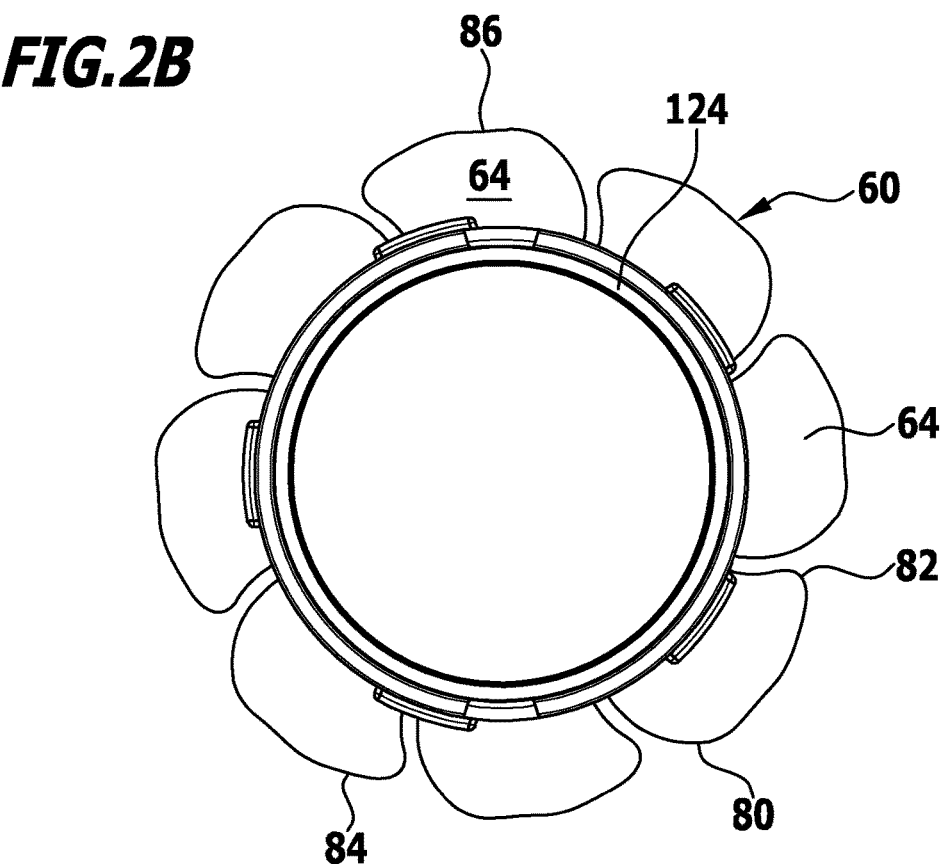
FIG. 2B shows a view of the protective device assuming the initial position in the direction of arrow A in FIG. 2A.
Figure 2C:
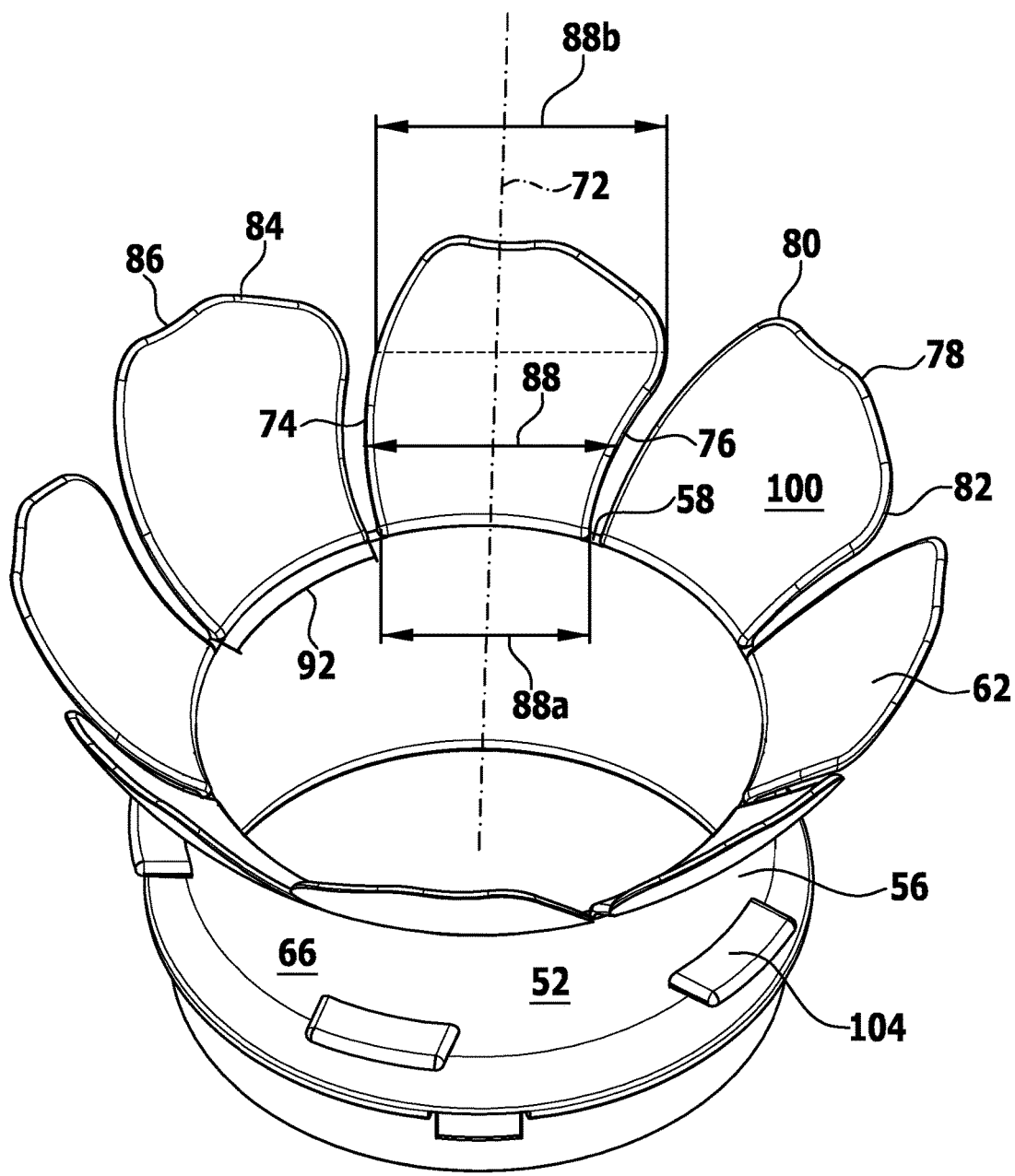
FIG. 2C shows a perspective view of the protective device assuming the initial position in FIG. 2A in the initial position.

The first ends 70 of the protective elements 60 define a circular arc segment 92 which defines an angular range corresponding to an angle that is slightly smaller than an eighth of 360° in the embodiment shown in FIGS. 2A to 2C.

In an area of transition 94 to the main body 52, the protective elements 60 are connected thereto in an articulated and/or hinge-like manner. Each protective element 60 is preferably connected to the main body 52 by a kind of film hinge 96. In particular, the articulated connection of the protective elements 60 to the main body 52 enables movement of the lamellas 62 from the initial position to a protective position by swiveling the lamellas in the direction towards the longitudinal axis 54.

Figure 3A:
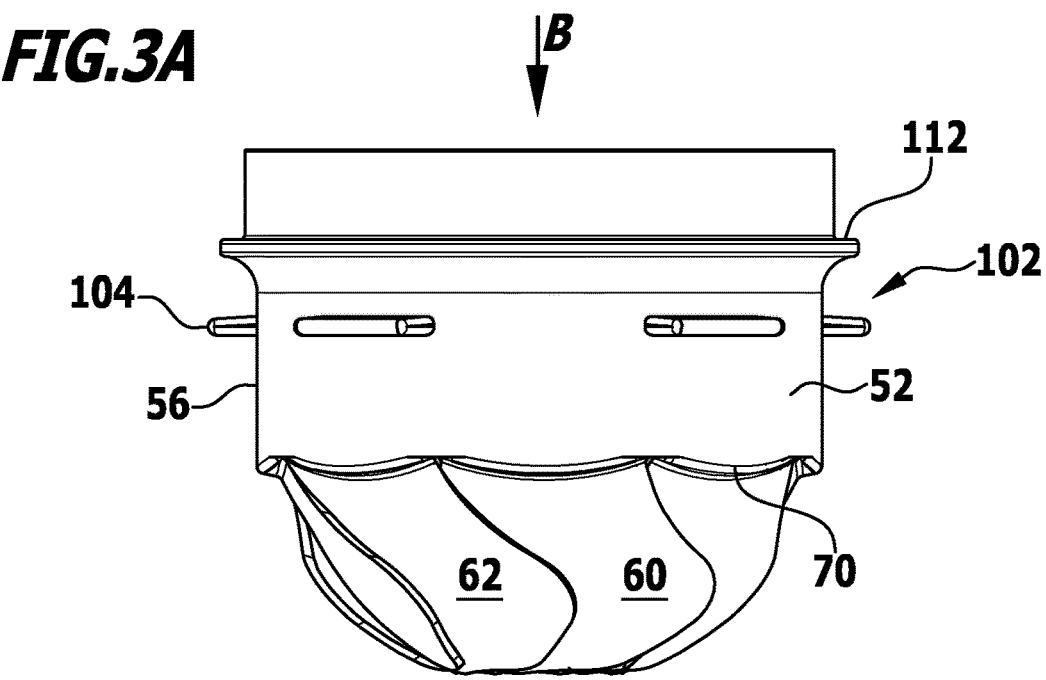
FIG. 3A shows a side view of a surgical protective device in a protective position.
Figure 3B:
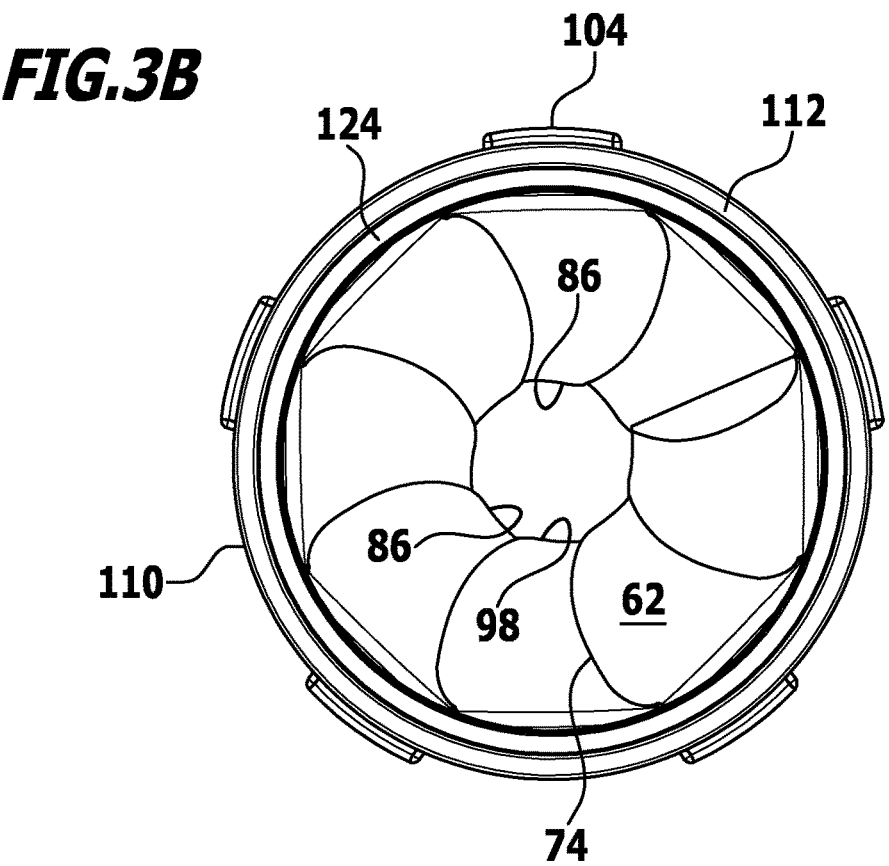
FIG. 3B shows a view of the protective device assuming the protective position in the direction of arrow B in FIG. 3A.
Figure 3C:
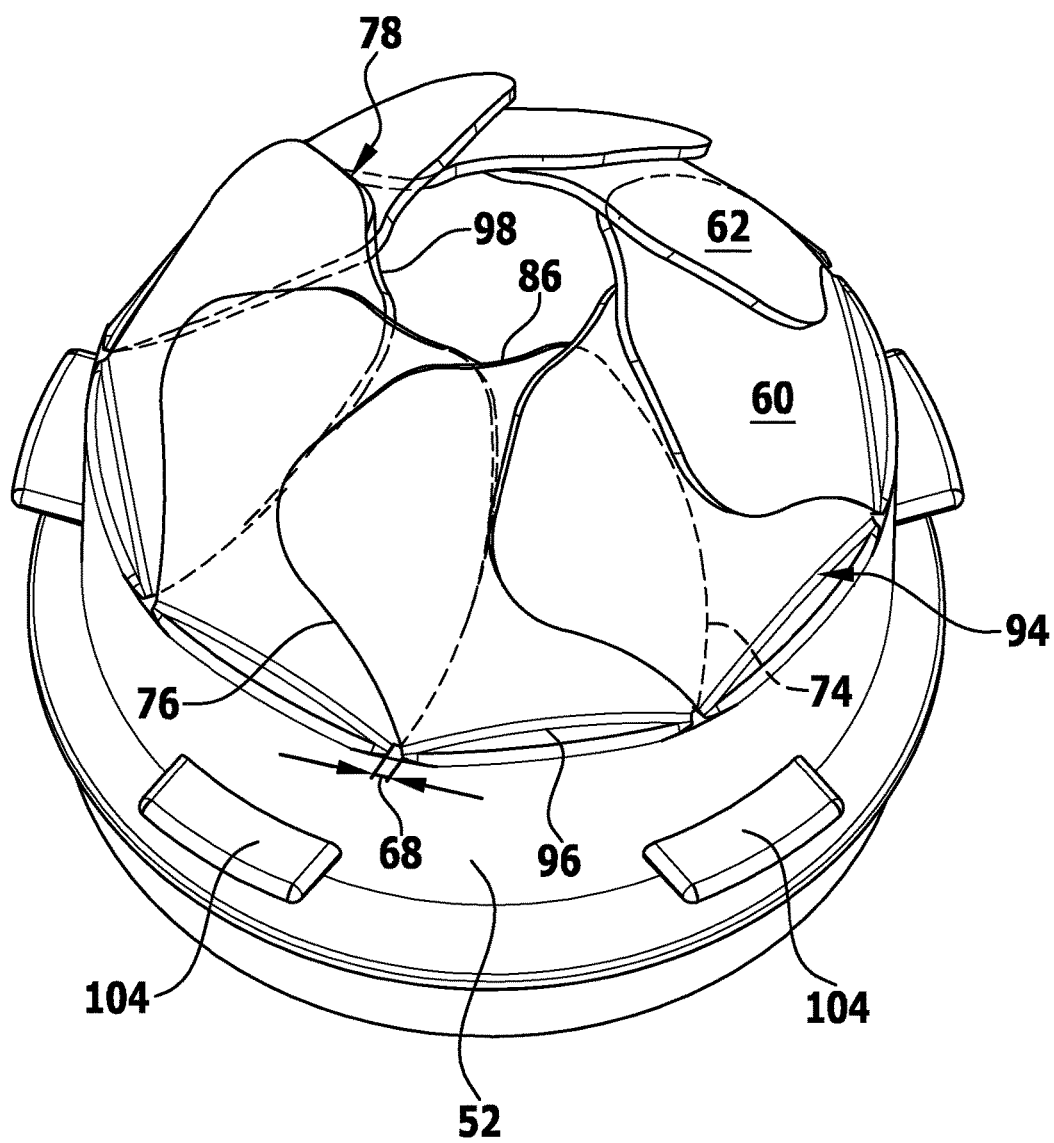
FIG. 3C shows a perspective view of the protective device from FIG. 2A assuming the protective position.

FIGS. 3A to 3C show schematically the protective device 50 in one of many possible protective positions, in which the protective elements 60 partially overlap. The schematically illustrated protective position defines a minimal opening 98 of the protective device 50, which is formed concentrically with the longitudinal axis 54, the edge sections 86 of the lamellas 62 swiveled in the protective position in the direction towards the longitudinal axis 54 each being oriented substantially concentrically with the longitudinal axis 54 and jointly forming the substantially circular opening 98. In this protective position, the lamellas 62 overlap in such a way that always only two layers of lamellas 62 lie on top of each other. This can be seen clearly, in particular, in FIG. 3C. The protective elements 60 overlap in such a way that the concave edges 76 abut on the outer sides 64 of the respective adjacent protective elements 60, the convex edges 74 on the inner sides 100 of the respective other adjacent protective elements 60.

In particular, instruments with shafts having a maximum outer diameter corresponding to an inner diameter of the sleeve 56 can be inserted through the protective device 50 from the proximal end. When inserting the shafts, the lamellas 62 are then correspondingly swiveled outwards, but still overlap slightly in the described manner so that at least the rounded parts 82 abut on the outer sides 64 of adjacent protective elements 60.

To ensure a defined position of the protective device 50 relative to the sealing element 36, the protective device 50 further comprises a connecting device 102 which has a total of five flange-like connecting projections 104 which point in the radial direction away from the longitudinal axis 54 and are spaced from one another in the circumferential direction. They are formed so as to correspond to connecting receptacles 107 in the area of a bulge-like thickening 106 on an inner side 108 of the sealing element 36.

Formed on the proximal side of the connecting projections 104 on the main body 52 is a ring-shaped flange 110 closed within itself having a flat ring surface 112 facing in the proximal direction, and a concavely curved delimiting surface 114 facing in the distal direction and slightly away from the longitudinal axis 54. As shown schematically in FIG. 4, the delimiting surface 114 abuts in the assembled state on a convexly curved ring surface 116 of the sealing element 36. The ring surface 116 is formed slightly to the proximal side of the thickening 106 and establishes the transition to a bellows-like protuberance 118, facing away from the longitudinal axis 54, of a wall 120 of the sealing element 36. Furthermore, the cover is provided with a ring surface 122 facing in the distal direction, which abuts on an end surface 124, facing in the proximal direction, of the main body 52 when the longitudinal axis 54 of the main body 52 is aligned coaxially with the longitudinal axis 12 of the sealing system 10.

In a protective position in which the lamellas 62 overlap to a maximum extent, as shown schematically in FIGS. 3A to 3C, in the undeflected state of the sealing element 36, the protective device 50 arranged in the sealing system 10 is arranged such that the opening 98 is positioned concentrically with the insertion opening 38 and extends practically as far as it. Therefore, in its initial position in which the insertion opening 38 is unexpanded, the sealing element 36 is optimally protected by the protective device 50.

Figure 6:
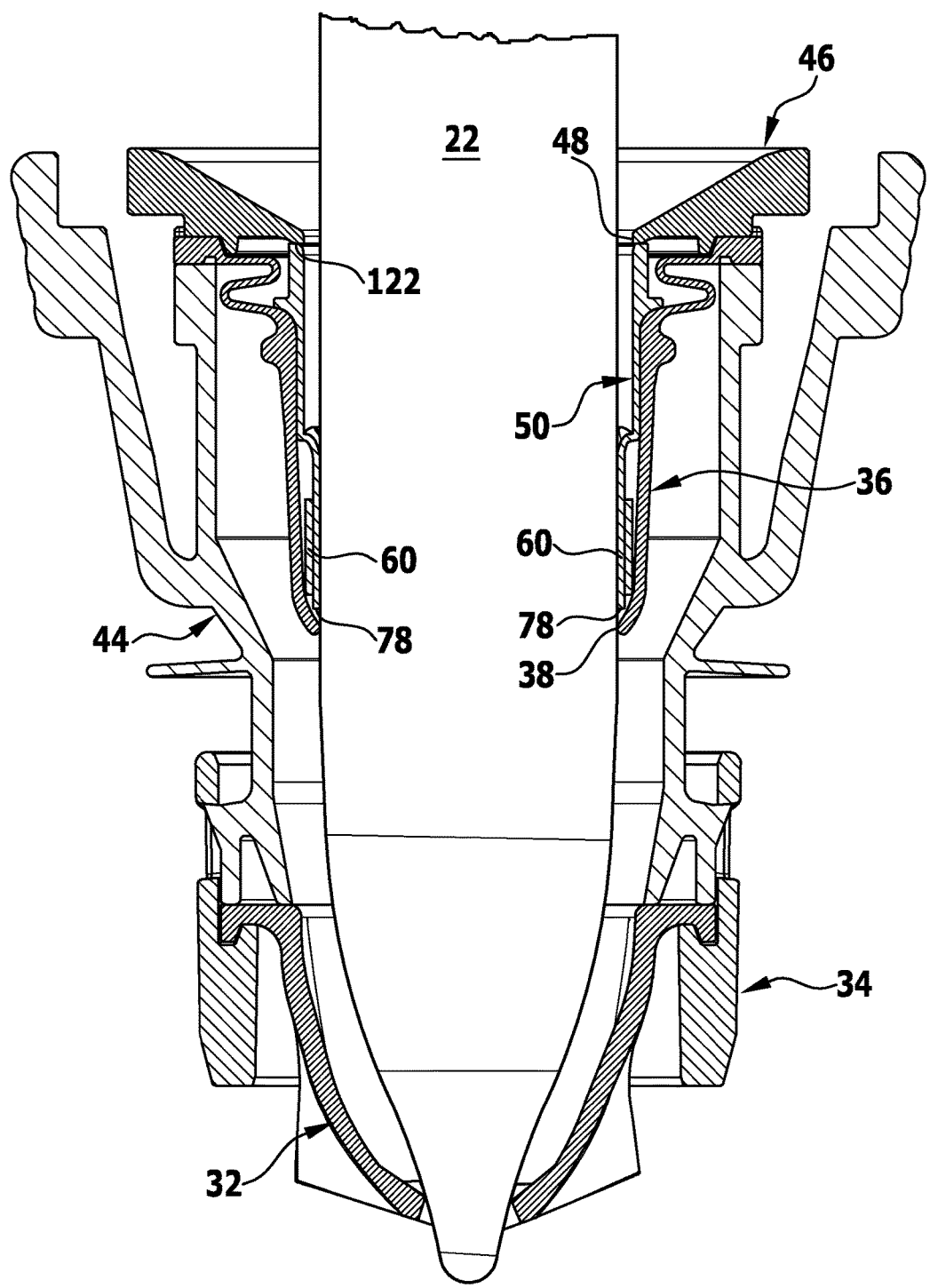
FIG. 6 shows a sectional view in analogy with FIG. 4 when inserting an obturator of the sealing system.

If a surgical instrument or, as shown schematically in FIG. 6, an obturator 22 is inserted from the proximal end through the opening 48 of the cover 46 and passed through the sealing element 36 and the cross-slot valve 32, the protective device 50 essentially prevents the instrument or the obturator from entering into direct contact with the sealing element 36. Damage to the sealing element 36 can thereby be practically prevented. During insertion, the instrument slides along the lamellas 62 and swivels these outwards away from the longitudinal axis 12. The lamellas 62 abutting with their outer sides 64 on the inner side 108 of the sealing element 36 take the sealing element 36 along with them and expand it, and the insertion opening 38 is also expanded at the same time.

Figure 4:
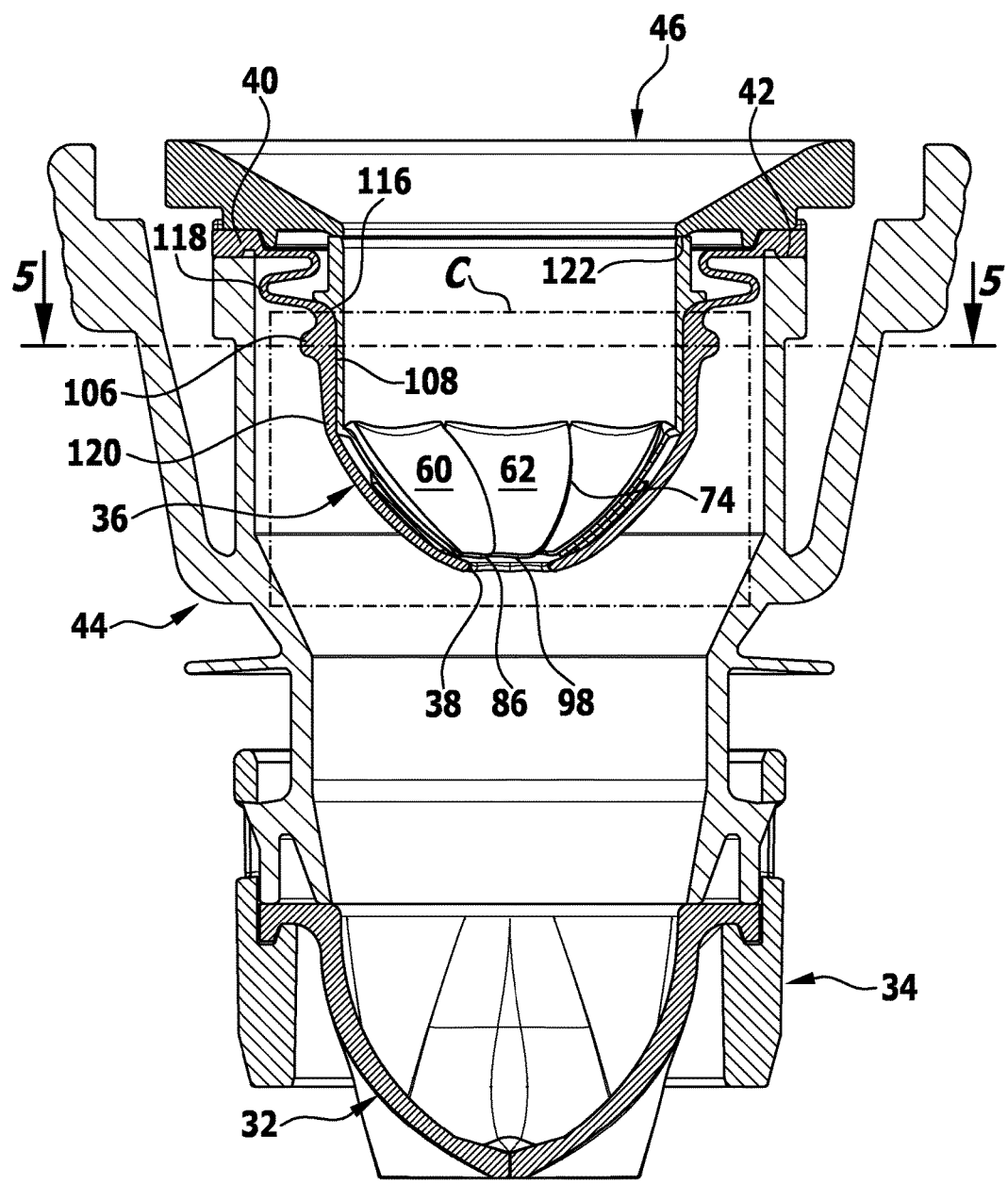
FIG. 4 shows a longitudinal sectional view of a sealing unit with sealing element retainer, sealing element, protective device and closing valve inserted in the trocar sleeve from FIG. 1.
Figure 5:
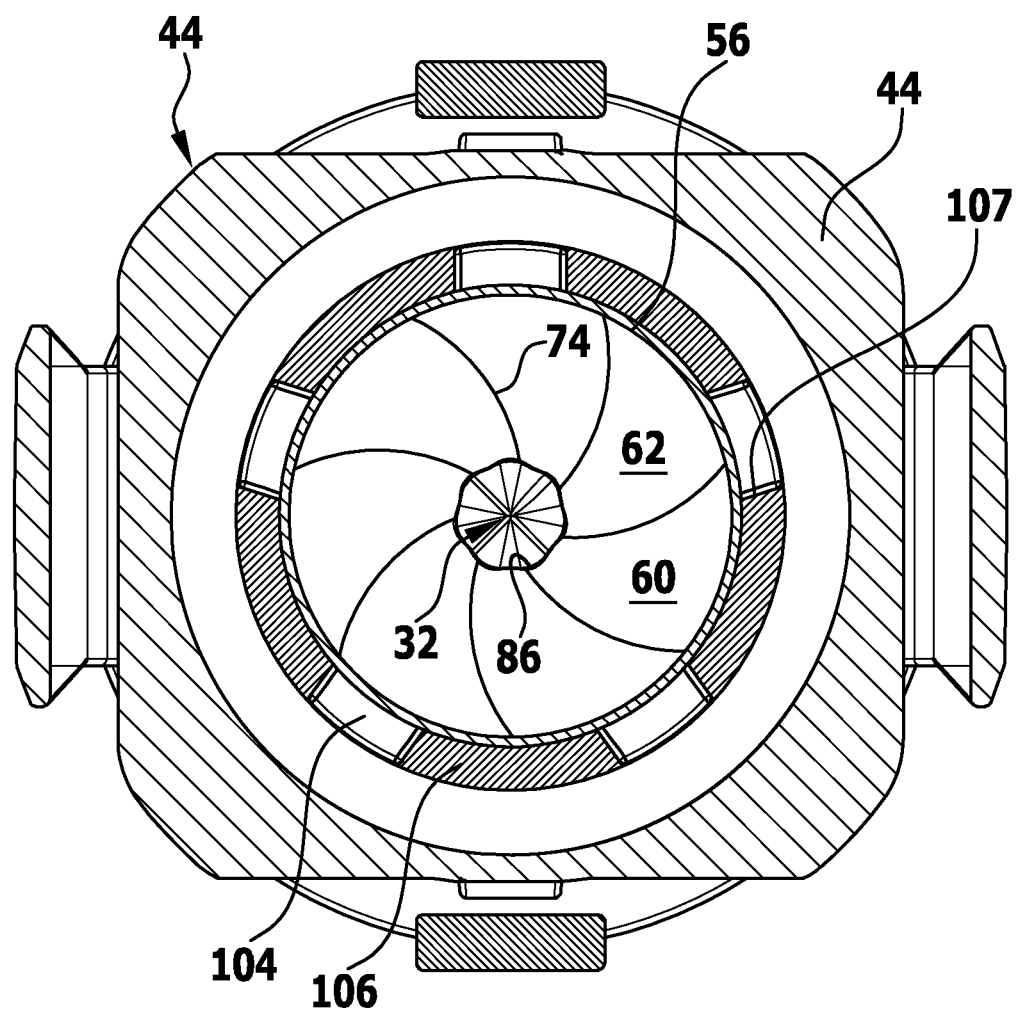
FIG. 5 shows a sectional view along line 5-5 in FIG. 4.

When the instrument is withdrawn from the sealing system 10, the prestressed sealing element 36 acts upon the protective elements 60 and swivels these back again into the protective position shown schematically in FIGS. 4 and 5, in which the insertion opening 38 is unexpanded or substantially unexpanded.

What is claimed is:
1. A surgical protective device for a surgical sealing element of a surgical sealing system comprising a trocar sleeve, the surgical sealing element having an expandable insertion opening, said protective device comprising:

a ring-shaped or substantially ring-shaped main body adapted to be arranged on the trocar sleeve, on a part of the trocar sleeve, or on the sealing element and defining a through-opening, and a plurality of protective elements arranged on the main body in a circumferential direction and extending parallel to or pointing towards a longitudinal axis of the protective device, wherein:

each of the protective elements is configured asymmetrically in relation to a plane containing a longitudinal axis defined by the main body, the protective device is of monolithic construction, the protective elements are separated from each other, the protective elements each have a first end which is arranged on an edge surface of the main body that faces in a distal direction with a spacing between the first ends of adjacent ones of the protective elements at the edge surface of the main body, each of the protective elements has two edges extending away from the first end, one of the two edges is convexly curved facing away from the protective element, and the other of the two edges is concavely curved facing away from the protective element.

2. The surgical protective device in accordance with claim 1, wherein the main body is configured substantially in the form of a ring-shaped sleeve.

3. The surgical protective device in accordance with claim 1, wherein the protective elements are slightly convexly curved in a direction facing away from the longitudinal axis.

4. The surgical protective device in accordance with claim 1, wherein the first ends of the protective elements at least one of: (a) define a circular arc segment; and (b) are arranged concentrically with the longitudinal axis.

5. The surgical protective device in accordance with claim 1, wherein the spacing between the first ends of the adjacent protective elements corresponds at least to at least one of a thickness of the protective elements and a thickness of the main body.

6. The surgical protective device in accordance with claim 1, wherein in an initial position after manufacture, the protective elements project in a radial direction facing away from the longitudinal axis over the edge surface facing in the distal direction.

7. The surgical protective device in accordance with claim 1, wherein the protective elements comprise lamellas having a thickness corresponding at the most to a thickness of a sleeve defining the main body.

8. The surgical protective device in accordance with claim 1, wherein all of the protective elements are identically constructed.

9. The surgical protective device in accordance with claim 1, wherein the protective elements have a second end facing away from the main body.

10. The surgical protective device in accordance with claim 9, wherein:

the second end at least one of: (a) extends between the two edges extending away from the first end; and (b) defines an end edge surface essentially having a slightly convexly curved basic shape facing away from the main body, and the end edge surface has a concavely curved edge section facing away from the main body.

11. The surgical protective device in accordance with claim 10, wherein:

adjacent protective elements overlap partially in a protective position, and the protective elements point in a direction towards the longitudinal axis in the protective position.

12. The surgical protective device in accordance with claim 11, wherein:

the protective elements, in the protective position, define at least one of: (a) a joint maximum inner diameter corresponding to an inner diameter of the main body; and (b) a minimal inner diameter when the protective elements partially overlap to a maximum extent, and the concavely curved edge sections of the end edge surfaces are aligned concentrically or substantially concentrically with the longitudinal axis.

13. The surgical protective device in accordance with claim 11, wherein the protective elements, in the protective position, irrespective of which inner diameter they define with their second ends, only overlap to such an extent that solely adjacent protective elements lie on top of each other.

14. The surgical protective device in accordance with claim 1, wherein the protective elements are connected in an area of transition in at least one of an articulated and a hinge-like manner to the main body.

15. The surgical protective device in accordance with claim 1, wherein the protective elements and the main body are connected to one another by a film hinge.

16. The surgical protective device in accordance with claim 1, further comprising a connecting device arranged on the main body for connecting the protective device to the surgical sealing element or to the surgical sealing system.

17. The surgical protective device in accordance with claim 1, wherein at least one of:

the protective elements have a constant thickness along their extent, the protective elements are of inherently flexible construction, the protective device is produced from a sterilizable material, and the protective device is produced from a plastic material.

18. A surgical sealing system, comprising:

a trocar sleeve, a surgical seal held on the trocar sleeve or on a part of the trocar sleeve and having an expandable insertion opening, for sealing the insertion opening upon insertion of a surgical instrument, and a surgical protective device for the seal, comprising:

a ring-shaped or substantially ring-shaped main body adapted to be arranged on the trocar sleeve, on a part of the trocar sleeve, or on the seal and defining a through-opening, and a plurality of protective elements arranged on the main body in a circumferential direction and extending parallel to or pointing towards a longitudinal axis of the protective device, wherein:

each of the protective elements is configured asymmetrically in relation to a plane containing a longitudinal axis defined by the main body the protective elements are separated from each other, the protective elements each have a first end which is arranged on an edge surface of the main body that faces in a distal direction with a spacing between the first ends of adjacent ones of the protective elements at the edge surface of the main body, each of the protective elements has two edges extending away from the first end, one of the two edges is convexly curved facing away from the protective element, and the other of the two edges is concavely curved facing away from the protective element.

19. A surgical sealing system for a trocar sleeve, comprising:

a surgical seal having an expandable insertion opening, for sealing the insertion opening upon insertion of a surgical instrument into the trocar sleeve, and a surgical protective device for the seal, comprising:

a ring-shaped or substantially ring-shaped main body arranged on the seal and defining a through-opening, and a plurality of protective elements arranged on the main body in a circumferential direction and extending parallel to or pointing towards a longitudinal axis of the protective device, wherein:

each of the protective elements is configured asymmetrically in relation to a plane containing a longitudinal axis defined by the main body, the protective elements are separated from each other, the protective elements each have a first end which is arranged on an edge surface of the main body that faces in a distal direction with a spacing between the first ends of adjacent ones of the protective elements at the edge surface of the main body, each of the protective elements has two edges extending away from the first end, one of the two edges is convexly curved facing away from the protective element, and the other of the two edges is concavely curved facing away from the protective element.

* * * * *